(12) United States Patent
Hon (10) Patent No.: US 8,365,742 B2
(45) Date of Patent: Feb. 5, 2013

(54) AEROSOL ELECTRONIC CIGARETTE

(75) Inventor: Lik Hon, Hong Kong (CN)

(73) Assignee: Ruyan Investment (Holdings) Limited, Hong Kong (HK)

( * ) Notice: Subject to any disclaimer, the term of this patent is extended or adjusted under 35 U.S.C. 154(b) by 0 days.

(21) Appl. No.: 13/079,937

(22) Filed: Apr. 5, 2011

(65) Prior Publication Data

US 2011/0209717 A1 Sep. 1, 2011

Related U.S. Application Data

(62) Division of application No. 12/226,818, filed as application No. PCT/CN2007/001575 on May 15, 2007.

(30) Foreign Application Priority Data

May 16, 2006 (CN) ...................... 2006 2 0090805 U (51) Int. Cl.
*A24F 47/00* (2006.01)
(52) U.S. Cl. .... 131/273; 131/194; 131/360; 128/202.21
(58) Field of Classification Search ............... 131/360, 131/194, 273; 128/202.21
See application file for complete search history.

(56) References Cited

U.S. PATENT DOCUMENTS

| | | |
|---|---|---|
| 1,775,947 A | 5/1927 | Robinson |
| 2,057,353 A | 10/1936 | Whittemore |
| 2,631,219 A | 3/1953 | Suchy |
| 3,200,819 A | 8/1965 | Gilbert |
| 4,171,000 A | 10/1979 | Uhle |
| 4,641,053 A | 2/1987 | Takeda |
| 4,735,217 A | 4/1988 | Gerth |
| 4,756,318 A | 7/1988 | Clearman |
| 4,771,796 A | 9/1988 | Myer |
| 4,819,665 A | 4/1989 | Roberts |
| 4,848,374 A | 7/1989 | Chard |
| 4,945,929 A | 8/1990 | Egilmex |
| 4,945,931 A * | 8/1990 | Gori |
| 4,947,875 A * | 8/1990 | Brooks |
| 5,042,470 A * | 8/1991 | Kanesaka |
| 5,060,671 A * | 10/1991 | Counts et al. |
| 5,080,114 A * | 1/1992 | Rudolph et al. |
| 5,095,921 A * | 3/1992 | Losee |
| 5,144,962 A * | 9/1992 | Counts |

(Continued)

FOREIGN PATENT DOCUMENTS

| | | |
|---|---|---|
| CN | 2047485 U | 11/1989 |
| CN | 1135860 | 11/1996 |

(Continued)

OTHER PUBLICATIONS

International Search Report issued Aug. 16, 2007 in corresponding PCT Application No. PCT/CN2007/001575 filed May 15, 2007, and English translation thereto, 6 pages.

(Continued)

*Primary Examiner* — Richard Crispino
*Assistant Examiner* — Dionne Walls Mayes
(74) *Attorney, Agent, or Firm* — Perkins Coie LLP (57) ABSTRACT

An aerosol electronic cigarette includes a battery assembly, an atomizer assembly and a cigarette bottle assembly and also includes a shell (a) which is hollow and integrally formed. Said battery assembly connects with said atomizer assembly and both are located in said shell (a). Said cigarette bottle assembly is located in one end of the shell (a), which is detachable. Said cigarette bottle assembly fits with said atomizer assembly. Said shell (a) has through-air-inlets (a1).

3 Claims, 8 Drawing Sheets

U.S. PATENT DOCUMENTS

| | | | |
|---|---|---|---|
| 5,159,940 A * | 11/1992 | Hayward et al. | |
| 5,190,060 A * | 3/1993 | Gerding | |
| 5,224,498 A | 7/1993 | Deevi | |
| 5,249,586 A * | 10/1993 | Morgan et al. | |
| 5,261,424 A * | 11/1993 | Sprinkel, Jr. | |
| 5,285,798 A * | 2/1994 | Banerjee | |
| 5,322,075 A * | 6/1994 | Deevi | |
| 5,388,594 A | 2/1995 | Counts | |
| 5,438,978 A | 8/1995 | Hardester | |
| 5,497,791 A | 3/1996 | Bowen et al. | |
| 5,505,214 A * | 4/1996 | Collins | |
| 5,591,368 A | 1/1997 | Fleischhauer et al. | |
| 5,666,977 A * | 9/1997 | Higgins | |
| 5,666,978 A * | 9/1997 | Counts | |
| 5,730,158 A | 3/1998 | Collins | |
| 5,743,251 A * | 4/1998 | Howell | |
| 5,799,663 A * | 9/1998 | Gross et al. | |
| 5,819,756 A * | 10/1998 | Mielordt | |
| 5,878,752 A * | 3/1999 | Adams et al. | |
| 5,894,841 A * | 4/1999 | Voges | |
| 6,040,560 A * | 3/2000 | Fleischhauer | |
| 6,041,789 A * | 3/2000 | Bankert | |
| 6,095,153 A | 8/2000 | Kessler | |
| 6,164,287 A * | 12/2000 | White | |
| 6,178,969 B1 * | 1/2001 | St. Charles | |
| 6,196,218 B1 * | 3/2001 | Voges | |
| 6,354,293 B1 | 3/2002 | Madison | |
| 6,357,671 B1 * | 3/2002 | Cewers | |
| 6,443,146 B1 * | 9/2002 | Voges | |
| 6,532,965 B1 * | 3/2003 | Abhulimen | |
| 6,715,494 B1 | 4/2004 | McCoy | |
| 6,772,756 B2 * | 8/2004 | Shayan | |
| 6,803,545 B2 * | 10/2004 | Blake | |
| 6,810,883 B2 * | 11/2004 | Felter | |
| 6,854,461 B2 * | 2/2005 | Nichols | |
| 6,854,470 B1 * | 2/2005 | Pu | |
| 7,100,618 B2 | 9/2006 | Dominguez | |
| 7,131,599 B2 | 11/2006 | Katase | |
| 7,726,320 B2 | 6/2010 | Robinson | |
| 7,832,410 B2 | 11/2010 | Hon | |
| 7,845,359 B2 | 12/2010 | Montaser | |
| 7,997,280 B2 | 8/2011 | Rosenthal | |
| 8,156,944 B2 | 4/2012 | Han | |
| 2003/0108342 A1 | 6/2003 | Sherwood et al. | |
| 2004/0261802 A1 | 12/2004 | Griffin et al. | |
| 2005/0016550 A1 | 1/2005 | Katase | |
| 2005/0236006 A1 | 10/2005 | Cowan | |
| 2006/0196518 A1 | 9/2006 | Hon | |
| 2008/0276947 A1 | 11/2008 | Martzel | |
| 2009/0095311 A1 | 4/2009 | Han | |
| 2009/0126745 A1 | 5/2009 | Hon | |
| 2009/0151717 A1 | 6/2009 | Bowen | |
| 2009/0188490 A1 | 7/2009 | Han | |
| 2009/0230117 A1 | 9/2009 | Fernando | |
| 2009/0260642 A1 | 10/2009 | Monsees | |
| 2009/0272379 A1 | 11/2009 | Thorens | |
| 2010/0031968 A1 | 2/2010 | Sheikh | |
| 2010/0126505 A1 | 5/2010 | Rinker | |
| 2010/0181387 A1 | 7/2010 | Zaffaroni | |
| 2010/0200008 A1 | 8/2010 | Taieb | |
| 2010/0242974 A1 | 9/2010 | Pan | |
| 2010/0307518 A1 | 12/2010 | Wang | |
| 2011/0005535 A1 | 1/2011 | Xiu | |
| 2011/0036346 A1 | 2/2011 | Cohen | |

FOREIGN PATENT DOCUMENTS

| | | |
|---|---|---|
| CN | 2293957 Y | 10/1998 |
| CN | 1252961 A | 5/2000 |
| CN | 03111582.9 | 11/2004 |
| CN | 1575673 A | 2/2005 |
| CN | 2719043 Y | 8/2005 |
| CN | 200420031182.0 | 8/2005 |
| CN | 2777995 Y | 5/2006 |
| CN | 200997909 Y | 1/2008 |
| CN | 101116542 A | 2/2008 |
| CN | 101176805 | 5/2008 |
| DE | 10051792 | 5/2002 |
| EP | 0057243 | 8/1982 |
| EP | 0230420 | 8/1987 |
| EP | 0295122 A2 | 12/1988 |
| EP | 0342538 | 11/1989 |
| EP | 0358002 | 3/1990 |
| EP | 0295122 B1 | 1/1992 |
| EP | 0545186 | 6/1993 |
| EP | 0703735 | 4/1996 |
| EP | 0824927 | 2/1998 |
| EP | 0845220 | 6/1998 |
| EP | 0893071 | 1/1999 |
| EP | 0951219 | 11/2002 |
| GB | 1528391 A | 10/1978 |
| JP | 64000498 | 1/1989 |
| JP | 06114105 | 4/1994 |
| JP | 07506999 | 8/1995 |
| JP | 09075058 | 3/1997 |
| UA | 47514 | 12/1997 |
| WO | WO9409842 | 5/1994 |
| WO | WO9421317 | 9/1994 |
| WO | WO9740876 | 11/1997 |
| WO | WO9748293 | 12/1997 |
| WO | WO9817130 | 4/1998 |
| WO | WO0049901 | 8/2000 |
| WO | WO0105459 | 1/2001 |
| WO | WO03034847 | 1/2003 |
| WO | WO03022364 | 3/2003 |
| WO | WO03055486 | 7/2003 |
| WO | WO03101454 | 12/2003 |
| WO | WO04001407 | 12/2003 |
| WO | WO2004023222 | 3/2004 |
| WO | WO2004080216 | 9/2004 |
| WO | PCT/CN04/000182 | 11/2004 |
| WO | PCT/CN05/000337 | 8/2005 |
| WO | WO2006082571 | 8/2006 |
| WO | WO2007078273 | 7/2007 |
| WO | WO2008077271 | 7/2008 |
| WO | WO2008130813 | 10/2008 |
| WO | WO2009118085 | 10/2009 |
| WO | WO2009135729 | 11/2009 |
| WO | WO2010052323 | 5/2010 |
| WO | WO2010091593 | 8/2010 |
| WO | 2010145468 | 12/2010 |
| WO | WO2010145805 | 12/2010 |
| WO | WO2011010334 | 1/2011 |
| WO | WO2011022431 | 2/2011 |

OTHER PUBLICATIONS

Australian Patent Office, Examination Report for SG 200505930-8, dated May 4, 2006.

Australian Patent Office; Exam Report for AU2004234199, dated Aug. 14, 2009.

Australian Patent Office; Search and Examination Report for SG200604498-6, dated Apr. 16, 2008.

China Intellectual Property Office, International Search Report for PCT/CN04/000182, dated Jun. 10, 2004.

China Intellectual Property Office, International Search Report for PCT/CN05/000337, Jul. 14, 2005.

China Intellectual Property Office, International Search Report for PCT/CN10/073613, Aug. 26, 2010.

China Intellectual Property Office, International Search Report for PCT/CN10/000125, Apr. 1, 2010.

*CN Creative ; Intellicig USA, Ruyan* v. *Smoking Everywhere et al.* CV11-6268 Invalidity Contentions, Apr. 12, 2012.

*Cyphert, Gil DBA NUIS, Ruyan* v. *Smoking Everywhere et al.* CV11-0367 Invalidity Contentions, Apr. 11, 2012.

European Patent Office, Supplemental Extended European Search Report for EP04718242, dated Jul. 27, 2007.

European Patent Office, Supplemental Extended European Search Report for EP05729107, dated Jul. 31, 2007.

European Patent Office, Supplemental Partial Extended European Search Report for EP05729107, dated May 22, 2007.

European Patent Office, Supplemental Partial Extended European Search Report for EP04718242, dated May 22, 2007.

Fin Branding Group, LLC, Request for Inter Partes Reexamination of U.S. Patent No. 8,156,944, filed Sep. 13, 2012.

Japanese Patent Office, Office Action and English Translation for JP2006504199, dated Oct. 30, 2009.
Korean Intellectual Property Office, Notice of Preliminary Rejection for KR1020057009767, dated Jul. 27, 2009.
Macau Patent Office, Official Communication for MOI121, dated Apr. 17, 2009.
Malaysian Patent Office, Examiner's Report for MY PI 20041407, dated Sep. 28, 2007.
*Sottera, Inc., Ruyan* v. *Smoking Everywhere et al.* CV11-0367 Invalidity Contentions, Apr. 12, 2012.
*Sottera, Inc., Ruyan* v. *Smoking Everywhere et al.* CV11-0367 Invalidity Contentions, Exhibit 7 (Claim 20 Claim Chart), Apr. 12, 2012.
*Sottera, Inc., Ruyan* v. *Smoking Everywhere et al.* CV11-0367 Invalidity Contentions, Exhibit 8 (Claim 24 Claim Chart), Apr. 12, 2012.
Taiwan Patent Office, Official Letter for TW093111573, dated Apr. 24, 2009.
Ukraine Patent Office, Examination Report for UA200511258, dated Feb. 4, 2009.
China Intellectual Property Office, English Translation of Written Opinion for PCT/CN07/001575, Jul. 20, 2007.
China Intellectual Property Office, English translation of Written Opinion for PCT/CN07/001576, Aug. 3, 2007.
China Intellectual Property Office, International Search Report for PCT/CN07/001576, Aug. 16, 2007.
China Intellectual Property Office, Search Report for CN ZL 200620090805.0.
Introduction to selecting and using electronic components, ISBN7-111-13752-3.
European Patent Office, Extended European Search Report for EP07721148, Dec. 6, 2010.
European Patent Office, Extended European Search Report for EP11001479, Jul. 4, 2011.
Manual for Electric Engineers, 2nd Ed, Mar. 2000.
Manual for Mechanical Designers, 4th Ed, Jan. 2002.
Materials Manual—Nonmetal, Jul. 1, 1985.
TechPowerUp "What is a MOSFET, what does it look like and how does it work?" May 24, 2004.
IP Australia, Patent Examination Report No. 1 for AU2007250367, Jul. 30, 2012.
IP Australia, Patent Examination Report No. 1 for AU2007250368, Aug. 9, 2012.
United States Patent and Trademark Office, Office Action in Inter Partes Reexamination of U.S. Patent No. 8,156,944, mailed Nov. 27, 2012.
Machine translation Chinese Patent Application 200420031182 which corresponds to the priority document of WO2005/099494 (Hon '494) Oct. 27, 2005, cited by the Examiner in the Nov. 27, 2012 Office Action identified above.
Machine translation of Chinese Patent Application 03111582.9 which corresponds to the priority document of WO2004/095955 (Hon '955) Nov. 11, 2004, cited by the Examiner in the Nov. 27, 2012 Office Action identified above.

* cited by examiner

AEROSOL ELECTRONIC CIGARETTE

BACKGROUND ART

Smoking causes serious respiratory system diseases and cancer, though it is hard to persuade the smokers to completely quit smoking.

Nicotine is the effective ingredient in cigarettes. Nicotine acts on the receptor of the central nervous system.

Nicotine is a micromolecular alkaloid, which is basically harmless to human bodies at a small dosage. Plus, its half life period is extremely short in blood. Tar is the major harmful substance in tobacco. Tobacco tar comprises several thousands of ingredients, dozens of which are carcinogenic substances.

To provide cigarette substitutes that contain nicotine but not harmful tar, many products have been used. These products are not as harmful as tar, but are absorbed very slowly. As a result, smokers can't be satisfied in full. In addition, the smokers are deprived of the "smoking" habit.

The electronic cigarettes currently available on the market may resolve the above-mentioned issue, though they are complicated in structure. They don't provide the ideal aerosol effects, and their atomizing efficiency is not high.

SUMMARY OF INVENTION

To overcome the above-mentioned disadvantages, an aerosol electronic cigarette includes a battery assembly, an atomizer assembly and a bottle assembly. The battery assembly connects with the atomizer assembly and both are located in a housing. The bottle assembly is located in one end of the housing and fits with the atomizer assembly.

The battery assembly may include the battery, an operating indicator, electronic circuit board, and airflow sensor, which are connected with the battery, and with the signal output of the airflow sensor connected the electronic circuit board.

A component for liquid storage of the cigarette bottle assembly stores the nicotine liquid. Smokers can enjoy the feel of smoking, with no fire hazard since there is no need for igniting.

SPECIFIC MODE FOR CARRYING OUT THE INVENTION

As shown in FIGS. 1-10, an aerosol electronic cigarette includes a battery assembly, an atomizer assembly and a cigarette bottle assembly, and also includes a shell or housing (a), which is hollow and integrally formed. The battery assembly connects with the atomizer assembly and both are located in the shell. The cigarette bottle assembly is located in one end of the shell, which is detachable. The cigarette bottle assembly fits with the atomizer assembly. The shell has through-air-inlets (a1).

Figure 1:
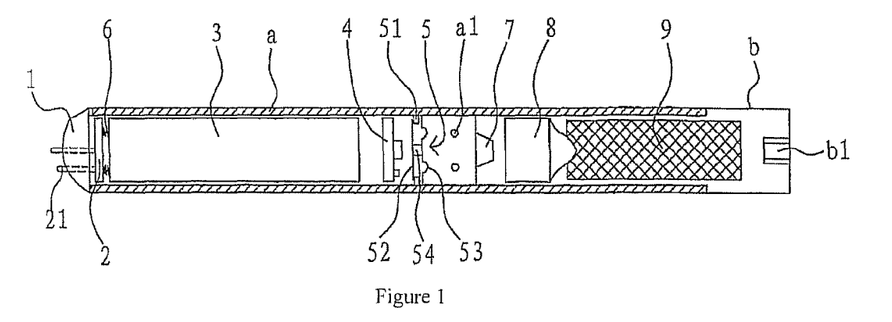
FIG. 1 is the side section view of an electronic cigarette.

In this specific embodiment, the battery assembly includes the battery, and the operating indicator (1), electronic circuit board (4), and airflow sensor (5), which are connected with the battery. It also includes a check valve (7). The signal output of the airflow sensor (5) is connected with the said electronic circuit board (4). The battery is a rechargeable battery (3), which may be either a rechargeable polymer lithium ion battery or a rechargeable lithium ion battery. The airflow sensor (5) may be alternatively a semiconductor force-sensitive chip capacitance sensor or an inductance sensor.

The rechargeable battery (3) has a flexibly connected charging plug (2). The blades (21) of the charging plug (2) come out of the other end of the shell (a). Between the charging plug (2) and rechargeable battery (3) is a spring (6), which lies against the body of the rechargeable battery (3) on one end, while its free end lies against the charging plug (2), forming a flexible structure, which buffers the charging plug (2) when plugged for charging, thus protecting the rechargeable battery against any damage. Of course, the rechargeable battery (3) in this embodiment has a charging slot on it, which replaces the structure of charging plug (2) to perform the charging function and protect the rechargeable battery (3) against any damage. The operating indicator (1) is a LED. In this embodiment, there are two LEDs. The electronic circuit board (4) includes an electronic switch circuit, which controls the electric circuit according to the input signals, so that the rechargeable battery (3) electrifies the electric heating rod (82) inside the atomizer (8) and the LEDs as well.

Figure 2:
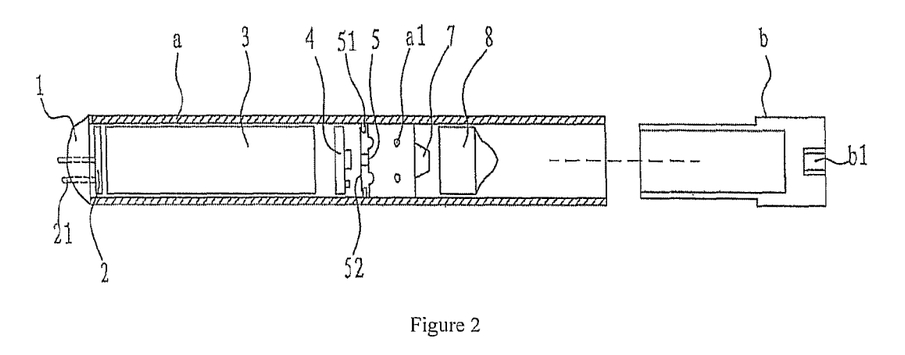
FIG. 2 is the section view of the housing (a) separated from the cigarette bottle assembly.

As shown in FIGS. 1 and 2, the airflow sensor (5) has a silica gel corrugated membrane (53), which connects with magnetic steel (54) with a reed relay (52) on one of its ends. Both ends of the said reed relay (52) correspond to the relay electrodes (51) respectively.

Figure 5:
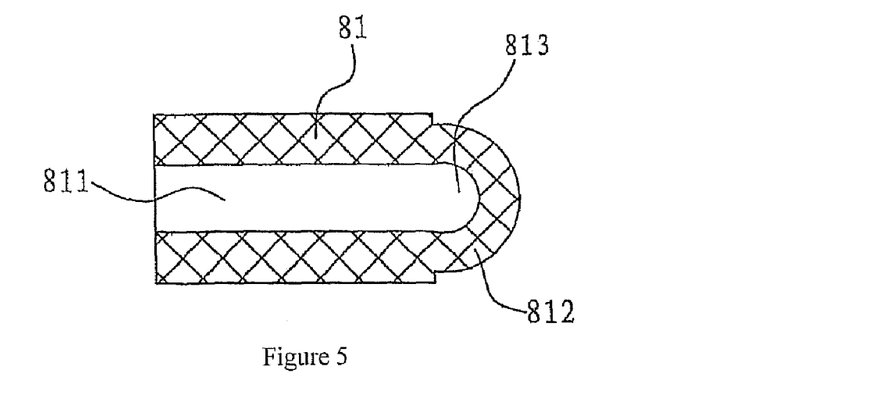
FIG. 5 is the side section view of a porous component of the atomizer.
Figure 6:
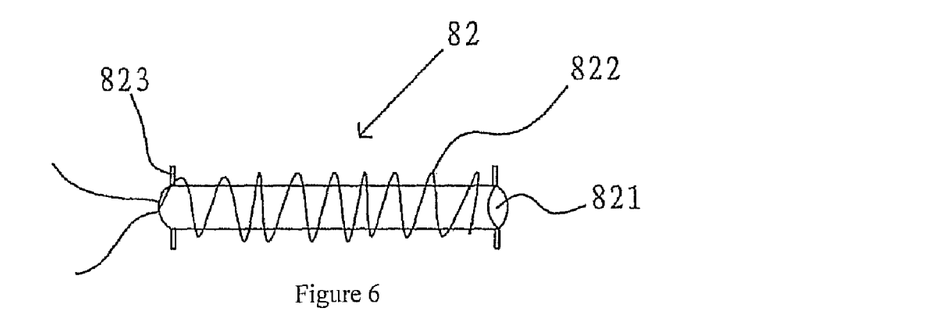
FIG. 6 is the diagram of the structure of an electric heating rod of the atomizer.
Figure 7:
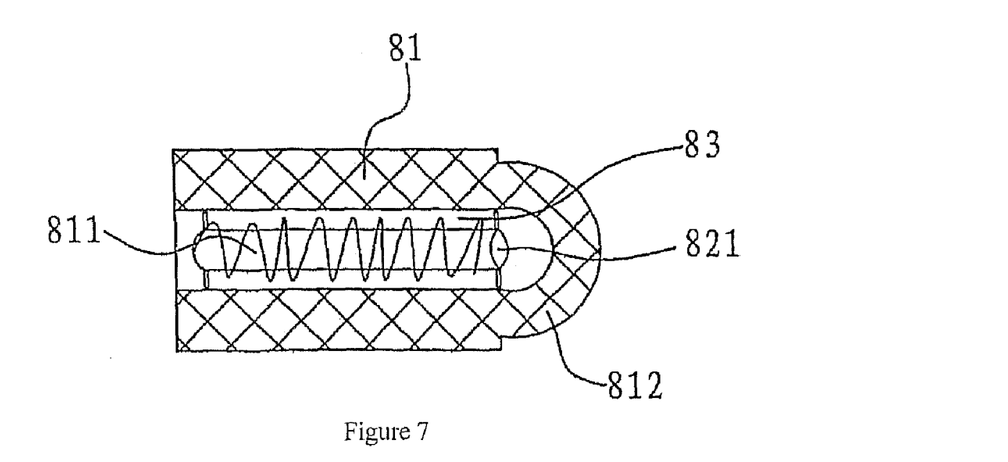
FIG. 7 is the side section of the atomizer, illustrating the locations of and connection relation between the electric heating rod and porous component.
Figure 8:
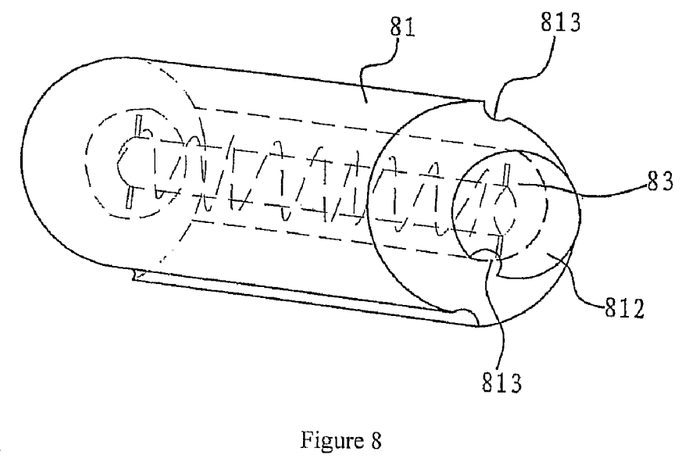
FIG. 8 is the diagram of the atomizer, illustrating the locations of and connection relation between the electric heating rod and porous component.
Figure 9:
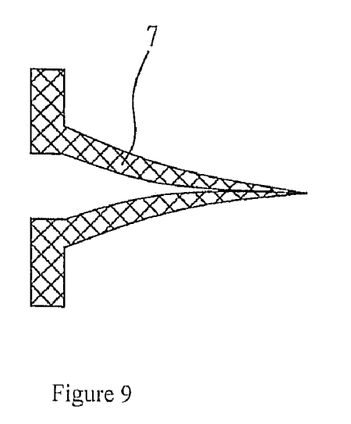
FIG. 9 is the section view of a check valve.

As shown in FIGS. 5-8, the atomizer assembly is an atomizer (8), which includes a porous component (81) and a heating rod (82). The body of the porous component (82) has a run-through atomizing chamber (811). The diameter of the electric heating rod (82) is less than the diameter of the atomizing chamber (811). The electric heating rod (82) enters into the atomizing chamber (811), and there is a clearance between the electric heating rod (82) and interior wall of the atomizing chamber (811), which forms a negative pressure cavity (83). One end of the porous component (81) fits with the cigarette bottle assembly. As FIGS. 5, 7 and 8 show, the porous component (81) has a protuberance (812) on the other end, and the protuberance (812) fits with the cigarette bottle assembly. The protuberance (812) is a protruding half sphere, on the side of which there is a run-through hole (813) connecting to the atomizing chamber (811). Of course, the protuberance (812) may also be a taper, rectangle or any other shape. The porous component (81) is made of foamed nickel, stainless steel fiber felt, macromolecular polymer foam or foamed ceramics, providing the remarkable capabilities in liquid absorption and diffusion, and the ability to absorb the liquid stored in the cigarette bottle assembly.

As shown in FIG. 6, the electric heating rod (2) includes a cylinder (821). The heating wire (822) is wound on the wall of the cylinder (821). On the wall of both ends of the cylinder (821), there are mandrils (823) respectively, which lie against the interior wall of the atomizing chamber (811) of the porous component (81). There is a negative pressure cavity (83) between the electric heating rod and interior wall of the atomizing chamber.

The heating wire is made of platinum wire, nickel-chromium alloy wire or iron-chromium alloy wire containing rare earth, or is flaked. The electric heating rod (82) may alternatively have on its peripheral wall the heating layer made of electrically conductive ceramic PTC material, to replace the heating wire.

In this embodiment, the battery assembly and atomizer assembly are mutually connected and then installed inside the integrally formed shell (a) to form a one-piece part. The rechargeable battery (3) may be charged without frequent change of battery. The user just needs to plug the cigarette bottle assembly into the open end of the shell (a), for easy use and very easy change.

Figure 3:
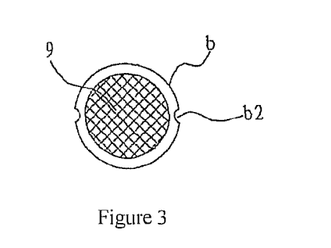
FIG. 3 is the diagram of the axial structure of the cigarette bottle assembly, illustrating the ventilating groove on the peripheral surface of the cigarette holder housing.
Figure 4:
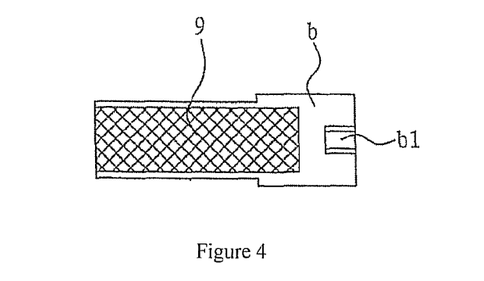
FIG. 4 is the side section view of the cigarette bottle assembly, illustrating the structure of the air channel.

As shown in 3 and 4, the cigarette bottle assembly includes a hollow cigarette holder shell (b), and a perforated component for liquid storage (9) inside the shell (b). The perforated component for liquid storage (9) is made of such materials as PLA fiber, terylene fiber or nylon fiber, which are suitable for liquid storage. Alternatively, it may be plastic foam molding or column of multi-layer plates made through plastic injection with polyvinyl chloride, ploypropylene and polycarbonate. One end of the cigarette holder shell (b) plugs into the shell (a), and the outer peripheral surface of the cigarette holder shell (b) has an inward ventilating groove (b2). On one end surface of the cigarette holder shell (b), there is an air channel (b1) extending inward. The air channel (b1) is located in the center on the surface of one end of shell (b).

As shown in FIGS. 1-9, one end of the porous component (81) lies against one end surface of the perforated component for liquid storage (9), and contacts the perforated component for liquid storage (9). It absorbs the cigarette liquid from the perforated component for liquid storage (9). When the smoker smokes, the cavity of the cigarette holder shell (b) is in the negative pressure state. In the shell (b), one end of the airflow sensor (5) forms a normal pressure cavity, while the other end forms a negative pressure cavity. The air pressure difference between the normal pressure cavity and negative pressure cavity or the high-speed airflow enables the magnetic steel (54) of the airflow sensor (5) to drive the reed relay (52) to contact the relay electrode (51).

Figure 20:
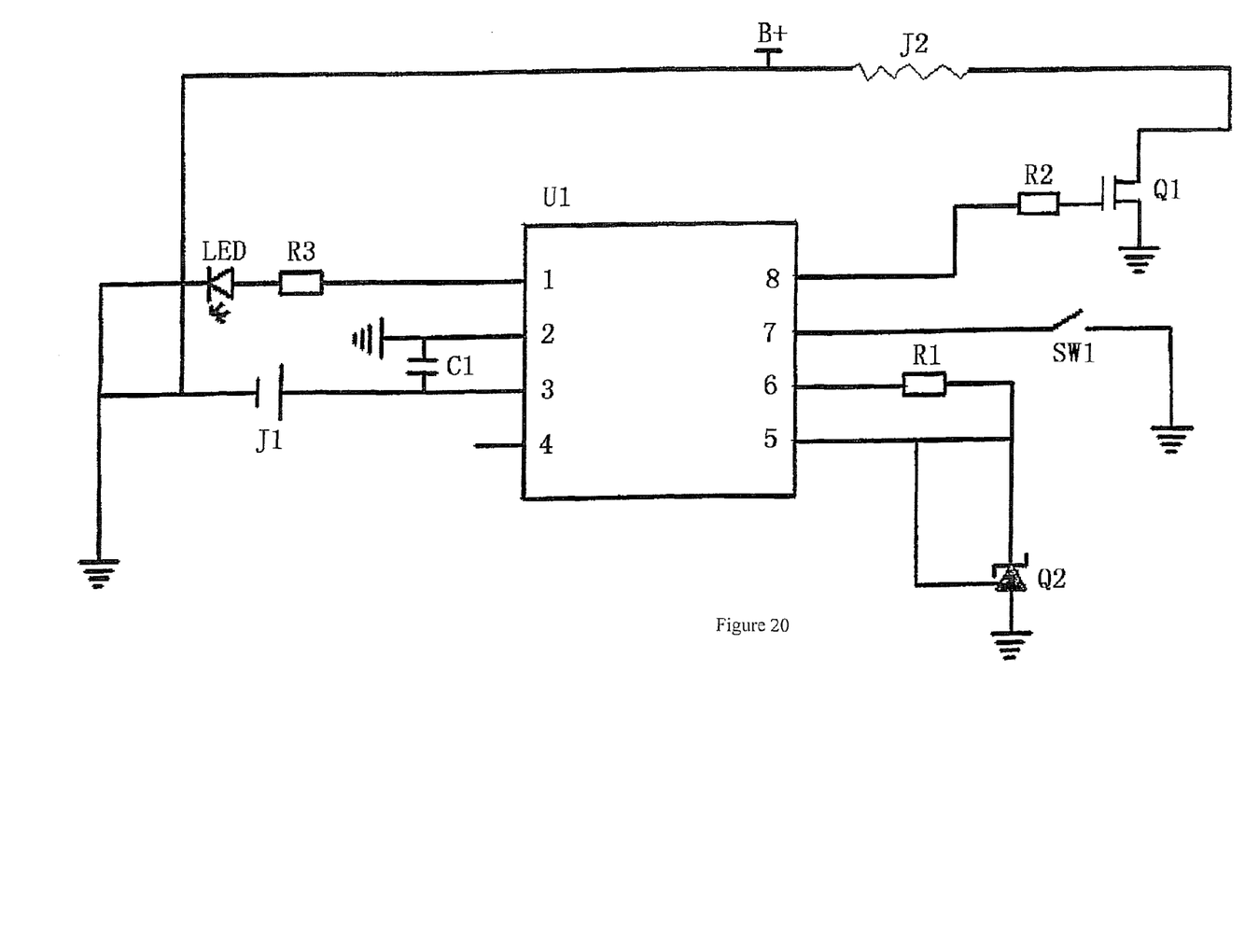
FIG. 20 is the electric circuit diagram of an electronic cigarette.

As shown in FIG. 20, the electric circuit is electrified, and the electronic switch circuit on the electronic circuit board (4) is electrified. Thus, the rechargeable battery (3) starts to electrify the electric heating rod (82) inside the atomizer (8), and at the same time, the LEDs, which are electrified by the rechargeable battery (3), emit light. The air enters the normal pressure cavity through the air inlet (a1), passes the check valve (7) via the airflow passage in the airflow sensor (5), and flows to the negative pressure cavity (83) in the atomizer (8). Since the negative pressure cavity (83) provides the negative pressure compared with the outside, the air flow sprays into it, bringing the cigarette liquid from the porous component (81) to spray into the negative pressure cavity (83) in the form of fine drops.

In the meantime, the electric heating rod (82) is electrified by the rechargeable battery (3) under the control of electronic circuit board (4), to heat the fine drips for atomization. After atomization, the big-diameter fine drips are re-absorbed by the porous component (81) under the action of vortex, while the small-diameter fine drips are suspended in the airflow to form aerosol, which is discharged through the negative pressure cavity (83) and run-through hole (813), flows into the cigarette holder shell (b) of the cigarette bottle assembly, and is absorbed by the air channel (b1). When the aerosol enters the cigarette holder shell (b), multiple small liquid drops are condensed into bigger ones, which fall into the clearance between the cigarette holder shell (b) and air channel (b1) without being absorbed by the air channel (b1). The perforated component for liquid storage (9) of the cigarette bottle assembly and the porous component (81) of the atomizer (8) contact each other to achieve the capillary impregnation for liquid supply.

The unit and its connecting structure of this invention may also be loaded with drugs for delivery to the lung.

Figure 22:
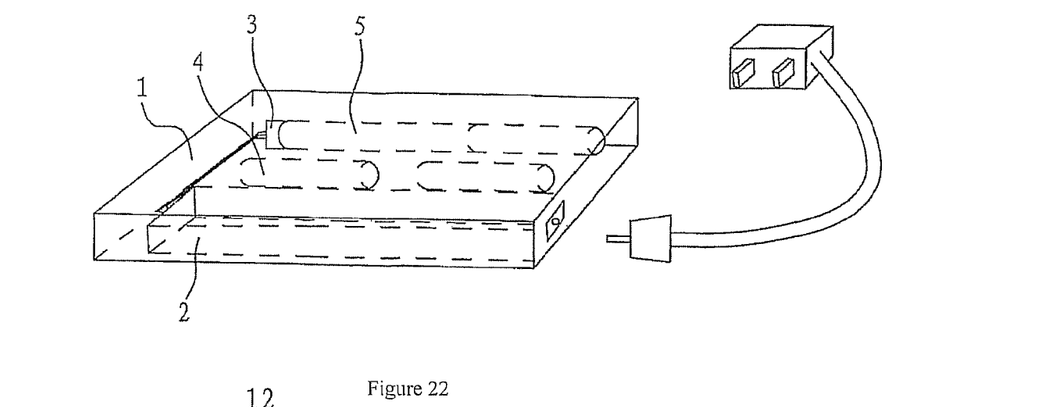
FIG. 22 is a diagram of a charging device, illustrating the locations of and connection relation of various internal parts.
Figure 23:
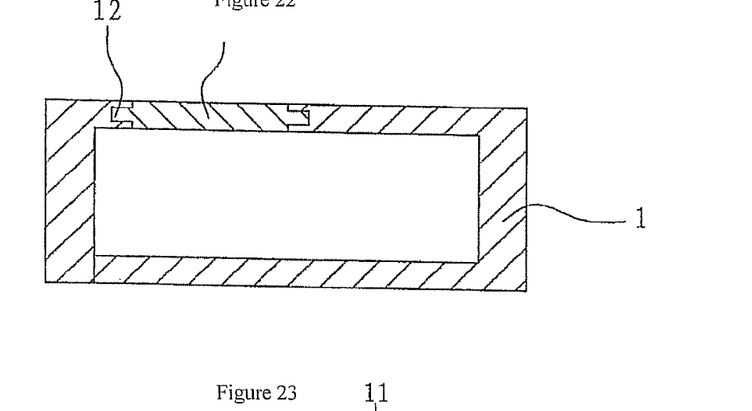
FIG. 23 is the side section view of the charging device.
Figure 24:
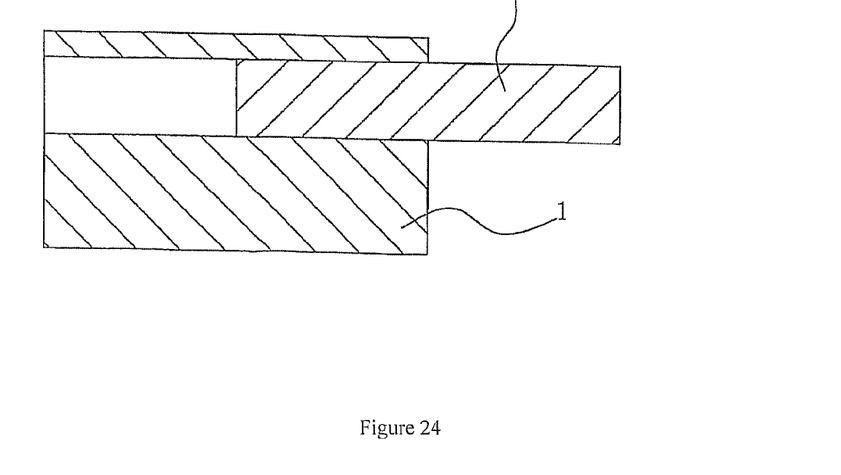
FIG. 24 is the diagram of the front structure of the charging device.

As shown in FIGS. 22, 23 and 24, the electronic cigarette (5) is held in a charging device. The charging device includes a case (1), which contains an auxiliary charging storage battery (2) inside it, and holds the electronic cigarette (5) and the charger (3) for the rechargeable battery embedded in the electronic cigarette (5), as well as the power supply circuit. The power inputs of the auxiliary charging storage battery (2) and charger (3) are connected with the power supply respectively. The charger (3) in this embodiment is a constant voltage & current charger. It may be a GY5210 charger, or any other constant voltage & current charger. The case (1) has a spare liquid supply bottle (4) in it. The power output of the auxiliary charging storage battery (2) is connected with the power input of the charger (3). The power output of the charger (3) is a charging slot (31), which fits with the charging plug of the rechargeable battery inside the electronic cigarette, or a charging plug, which fits with the charging slot of the rechargeable battery.

As shown in FIGS. 23 and 24, on the body of the shell (1), there is a pair of slide ways (12) corresponding to the position of the electronic cigarette, and on the slide ways, there is a slide cover (11).

Figure 10:
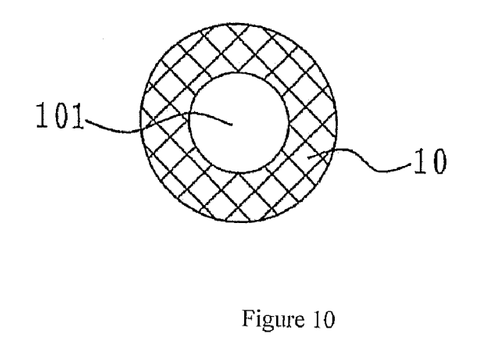
FIG. 10 is the front section view of a restriction component in a second embodiment.

In the second preferred embodiment, a restriction component (10), which is detachable, is set on one end of the porous component (81). There is a restriction hole (101) on the body of the restriction component (10). The restriction hole (101) corresponds to the atomizing chamber (811). The pore diameter of the restriction hole is less than the inner diameter of the atomizing chamber (811) to the extent that the size of the restriction component (10) installed on the porous component (81) varies, for the purpose of airflow capacity control. On the basis of different applications, the restriction component of different sizes and pore diameters may be used.

Figure 11:
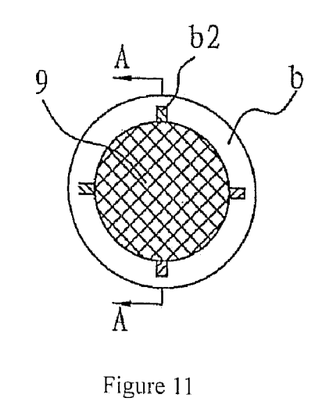
FIG. 11 is a diagram of the axial structure of the cigarette bottle assembly in another embodiment.
Figure 12:
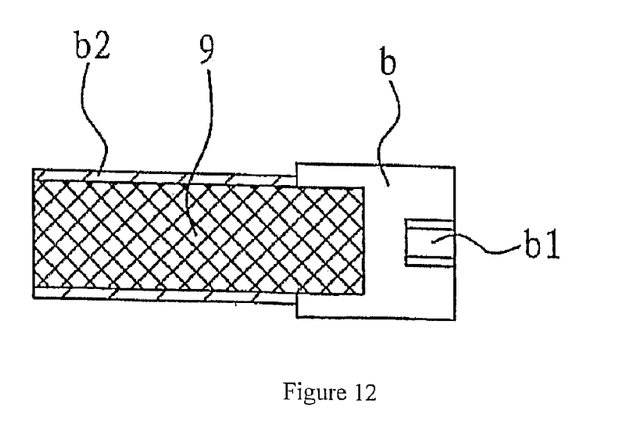
FIG. 12 is a sectional view taken along line A-A of FIG. 11.
Figure 13:
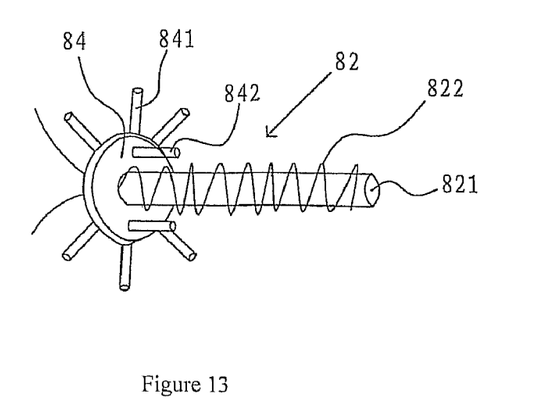
FIG. 13 is a diagram of the structure of the electric heating rod of the atomizer in another embodiment.
Figure 14:
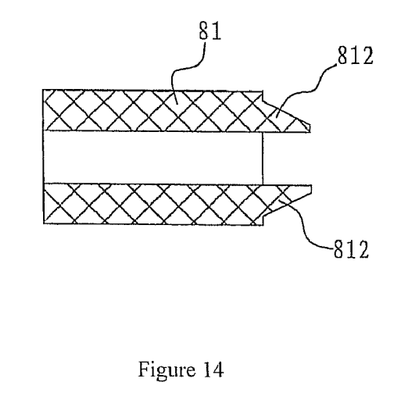
FIG. 14 is a section view of the porous component of the atomizer in the embodiment shown in FIG. 13.
Figure 15:
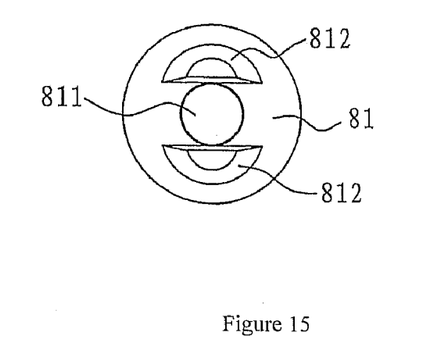
FIG. 15 is a diagram of the axial structure of FIG. 14.
Figure 16:
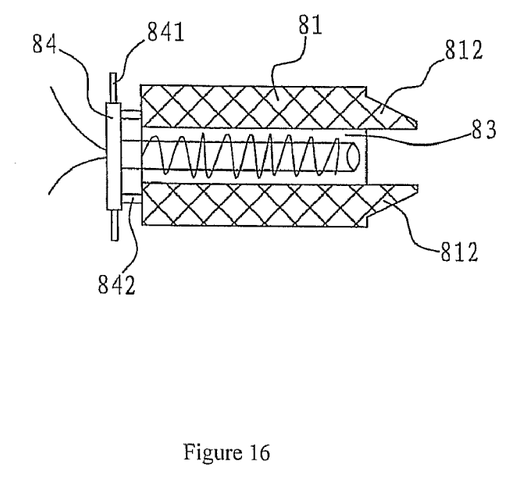
FIG. 16 is a side section view of the atomizer in the embodiment of FIG. 13, illustrating the locations of and connection relation between the electric heating rod and porous component.

In the third preferred embodiment of this utility model, as shown in 11 and 12, on the outer peripheral wall of the cigarette shell (b), there is a protruding rib (b2) that is evenly partitioned. The perforated component for liquid storage (9) enters the cigarette holder shell (b) and lies against the protruding rib (b2). Thus, there appears a clearance between the outer peripheral surface of the perforated component for liquid storage (9) and the interior wall of the shell (b). The clearance is for connection the shell (a) and cigarette holder shell (b). When the user smokes, the air channel (b1) absorbs the air to cause airflow inside the shell (a), thus triggering the airflow sensor (5) and eventually starting the electronic cigarette. Also, the atomizer (8) works to atomize the cigarette liquid and produce gas flow, which enters the cigarette holder shell (b).

In the fourth preferred embodiment, as shown in FIGS. 13, 14, 15 and 16, on one end of the cylinder (821), there is a fixed plate (84), whose outer peripheral wall has partitioned supports (841). The outer ends of the supports (841) lie against the interior wall of the shell (a), thus suspending the cylinder (821), which is connected with the fixed plate (84), in the cavity of the shell (a). On the surface of the fixed plate (84), there is a mandril (842), whose front end lies against one end of the porous component (81), so that the fixed plate (84) is separated from the atomizing chamber (811) of the porous component (81). As a result, the run-through hole on one end of the atomizing chamber (811) won't be blocked, and the mist generated in the atomizing chamber (811) can be dispersed. One end of the porous component (81) has two protuberances (812) at the outlet of the atomizing chamber (811). Between the two protuberances (812) is a clearance. The two protuberances (812) lie against the perforated component for liquid storage (9).

Figure 17:
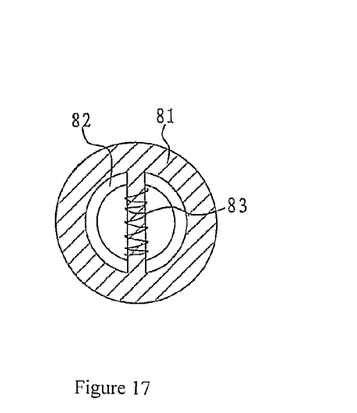
FIG. 17 is a diagram of the axial structure of the atomizer in another embodiment.
Figure 18:
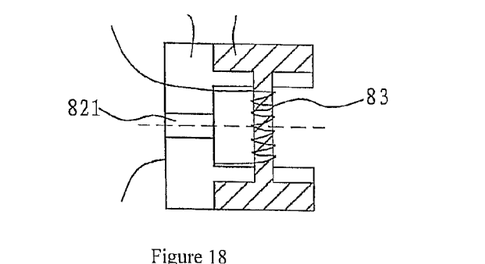
FIG. 18 is the side section view of the atomizer shown in FIG. 17.

In the fifth preferred embodiment, as shown in FIGS. 17 and 18, the atomizer assembly is an atomizer (8), which includes a frame (82), the porous component (81) set on the frame (82), and the heating wire (83) wound on the porous component (81). The frame (82) has a run-through hole (821) on it. The porous component (81) is wound with heating wire (83) in the part that is on the side in the axial direction of the run-through hole (821). One end of the porous component (81) fits with the cigarette bottle assembly. The porous component (81) is made of foamed nickel, stainless steel fiber felt, macromolecular polymer foam or foamed ceramics.

Figure 19:
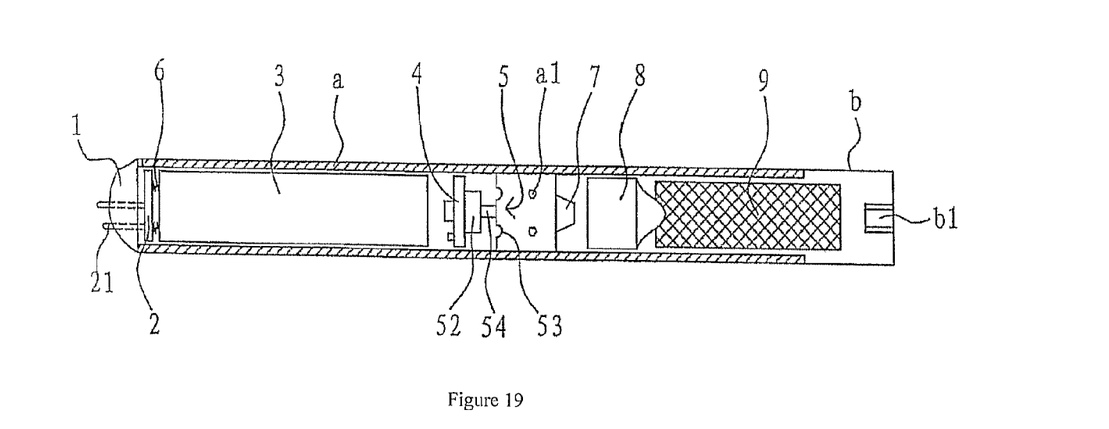
FIG. 19 is the side section view of another electronic cigarette embodiment.
Figure 21:
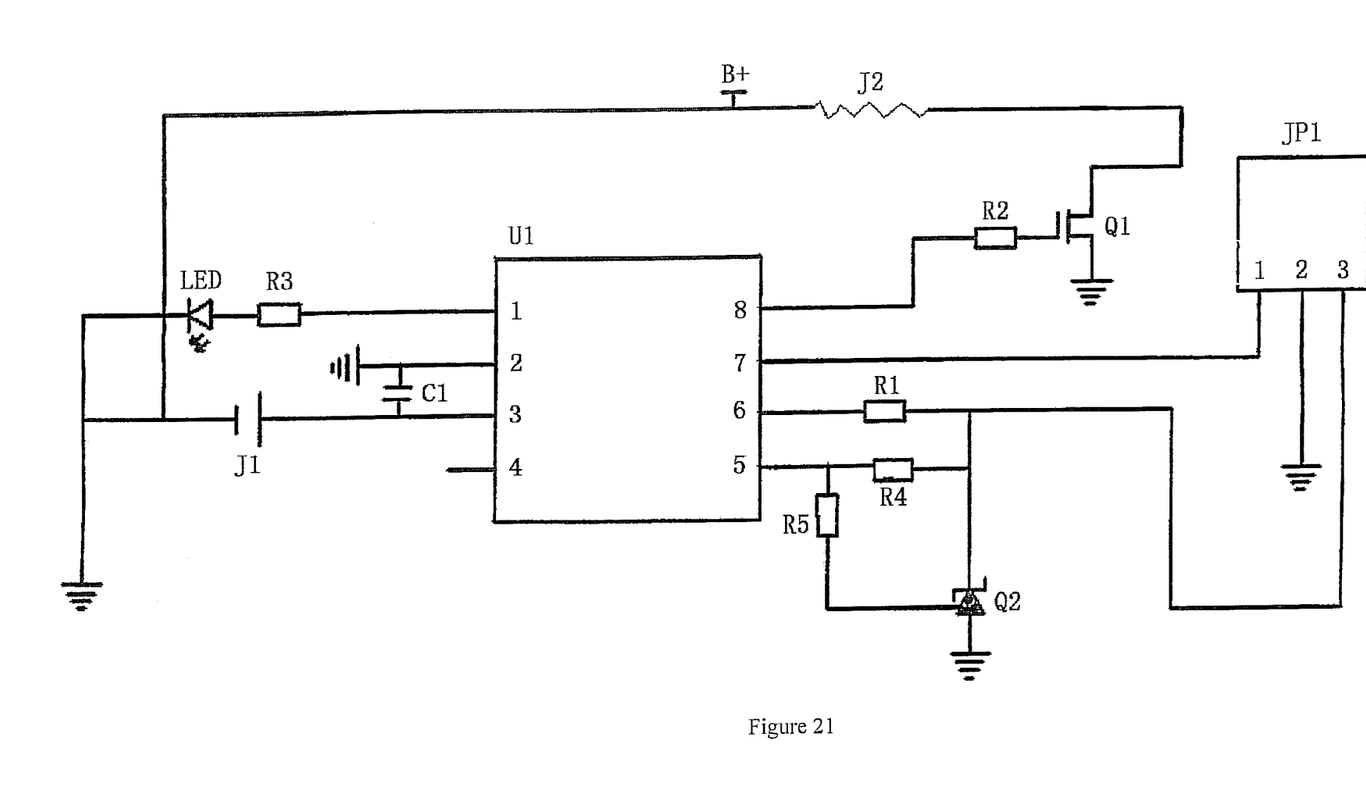
FIG. 21 is another electric circuit diagram of an electronic cigarette.

In the sixth preferred embodiment, as shown in FIG. 19, the airflow sensor (5) has a silica gel corrugated membrane (53), which connects with magnetic steel (54) with a Hall element (52), or a magneto-diode or a magneto-triode on one of its ends. FIG. 21 shows the electric circuit of the electronic cigarette of this solution.

What is claimed is:

1. An aerosol electronic cigarette, comprising:
a battery assembly, an atomizer assembly and a cigarette bottle assembly, and a shell that is hollow and integrally formed;
the battery assembly electrically connected with the atomizer assembly, and both are located in the shell;
the cigarette bottle assembly is detachably located in one end of the shell, and fits with the atomizer assembly inside it;
the shell has through-air-inlets;
the atomizer assembly is an atomizer, which includes a porous component and a heating body;
the heating body is heating wire;
the atomizer includes a frame;
the porous component is supported by the frame;
the heating wire is wound on the porous component;
the frame has a run-through hole;
a heating wire wound on a part of the porous component that is substantially aligned with the run-through hole; and with the porous component also positioned substantially within the cigarette bottle assembly.

2. An electronic cigarette, comprising:
a battery assembly and an atomizer assembly within a housing with the battery assembly electrically connected to the atomizer assembly;
a liquid storage component in the housing;
with the housing having one or more through-air-inlets;
the atomizer assembly including a porous component supported by a frame having a run-through hole;
a heating wire wound on a part of the porous component in the path of air flowing through the run-through hole; and
the porous component substantially surrounded by the liquid storage component.

3. An electronic cigarette, comprising:
a battery assembly and an atomizer assembly within a housing with the battery assembly electrically connected to the atomizer assembly;
with the housing having one or more through-air-inlets and an outlet;
the atomizer assembly includes a frame having a run through hole, and a porous component between the frame and the outlet;
a heating wire wound on a part of the porous component which is substantially aligned with the run-through hole; and
with the porous component in contact with a liquid supply in the housing.

* * * * *

UNITED STATES PATENT AND TRADEMARK OFFICE
CERTIFICATE OF CORRECTION

PATENT NO. : 8,365,742 B2  
APPLICATION NO. : 13/079937  
DATED : February 5, 2013  
INVENTOR(S) : Lik Hon Page 1 of 1

It is certified that error appears in the above-identified patent and that said Letters Patent is hereby corrected as shown below:

On the Title page, in Item (54), under "Title", in column 1, line 1, and in specification, column 1, line 1, delete "AEROSOL ELECTRONIC CIGARETTE" and insert -- ELECTRONIC CIGARETTE --, therefor.

In the Specifications:

In column 1, line 2, below "Title" insert -- This application is divisional of U.S. Patent Application No. 12/226,818, filed Oct. 29, 2008, which is the U.S. national stage application to International Patent Application No. PCT/CN2007/001575, filed on May 15, 2007, which claims priority, under 35 U.S.C. § 119, to Chinese Patent application No.: 200620090805.0, filed on May 16, 2006, the disclosures of which are incorporated by reference herein in their entireties. --.

In column 3, line 28, delete "(2)" and insert -- (82) --, therefor.

In column 3, line 49, after "shown in" insert -- FIGS. --.

In column 3, line 56, delete "ploypropylene" and insert -- polypropylene --, therefor.

In the Claims:

In column 6, lines 45-46, in claim 3, delete "run through" and insert -- run-through --, therefor.

Signed and Sealed this  
Second Day of July, 2013

Teresa Stanek Rea  
*Acting Director of the United States Patent and Trademark Office*